United States Defensive Publication [19] (H) [11] T100,403

Shepherd [43] Mar. 3, 1981

[54] HYPOLIPIDEMIC AND ANTI-ATHEROSCLEROTIC 2- OR 3-(MONOSUBSTITUTED-AMINO) PHENYL COMPOUNDS

[75] Inventor: Robert G. Shepherd, South Nyack, N.Y.

[73] Assignee: American Cyanamid Company, Stamford, Conn.

[21] Appl. No.: 85,650

[22] Filed: Oct. 17, 1979

[51] Int. Cl.[3] ..... A61K 31/195

[52] U.S. Cl. ..... 424/319; 260/345.8 R; 260/348.59; 424/263; 424/267; 424/270; 424/278; 424/283; 424/307; 424/310; 424/324; 546/226; 546/350; 548/201; 560/19; 560/50; 562/458; 568/424; 564/91; 564/99; 564/149; 564/157; 564/163; 564/167

[57] ABSTRACT

Hypolipidemic and anti-atherosclerotic 2- or 3-(monosubstituted-amino) phenyl compounds of the formulae:

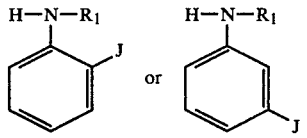

wherein $R_1$ is a saturated or unsaturated hydrocarbon radical of 8–19 carbon atoms which may be branched or unbranched and which may contain one or more radicals selected from the group consisting of saturated or unsaturated cycloalkyl, substituted or unsubstituted aryl and substituted or unsubstituted heteroaryl; J is

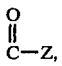

wherein Z is inter alia hydrogen, loweralkyl, hydroxy, loweralkoxy and loweralkoxyalkoxy, or J is carboxyloweralkyl, carboxyloweralkenyl, carboxyloweralkynyl, carboalkoxyloweralkyl, carboalkoxyloweralkenyl or carboalkoxyloweralkynyl.

29 Claims, No Sheets Drawing,

52 Pages Specification

The file of this unexamined application may be inspected and copies thereof may be purchased (849 O.G. 1221, Apr. 9, 1968).